United States Patent [19]

Rosini et al.

[11] Patent Number: 4,814,326

[45] Date of Patent: Mar. 21, 1989

[54] PHARMACEUTICAL COMPOSITIONS BASED ON DIPHOSPHONATES FOR THE TREATMENT OF ARTHROSIS AND OSTEOARTHRITIS

[75] Inventors: Sergio Rosini; Luciano Fontanelli, both of Pisa, Italy

[73] Assignee: Istituto Gentili S.p.A., Mazzini, Italy

[21] Appl. No.: 127,191

[22] Filed: Dec. 1, 1987

Related U.S. Application Data

[63] Continuation-in-part of Ser. No. 866,235, May 22, 1986, abandoned.

[30] Foreign Application Priority Data

May 24, 1985 [IT] Italy ................. 67478 A/85

[51] Int. Cl.$^4$ .............. A61K 31/045; A61K 31/13; A61K 31/195; A61K 31/66
[52] U.S. Cl. .............. 514/108; 260/502.4 R; 260/502.5 C
[58] Field of Search ....................... 514/108

[56] References Cited

U.S. PATENT DOCUMENTS

| | | | |
|---|---|---|---|
| 3,422,021 | 1/1969 | Roy | 260/502.4 P |
| 3,422,137 | 1/1969 | Quimby | 260/502.4 P |
| 3,471,406 | 10/1969 | Budnick | 260/502.4 P |
| 3,584,124 | 6/1971 | Francis | 514/108 |
| 3,962,432 | 6/1976 | Schmidt-Dunker | 514/108 |
| 4,230,700 | 10/1980 | Francis | 514/108 |
| 4,330,530 | 5/1982 | Baker | 514/108 |
| 4,446,052 | 5/1984 | Sunbery et al. | 514/108 |

FOREIGN PATENT DOCUMENTS

| | | | |
|---|---|---|---|
| 0088462 | 9/1983 | European Pat. Off. | 514/108 |
| 1421064 | 1/1976 | United Kingdom | 514/108 |
| 2096889 | 10/1982 | United Kingdom | 514/108 |

*Primary Examiner*—J. E. Evans
*Attorney, Agent, or Firm*—Bucknam and Archer

[57] ABSTRACT

This invention relates to pharmaceutical compositions for the treatment of arthrosis by intraarticular administration of the compositions diluted in a suitable aqueous or lyophilized carrier, comprising an effective amount of diphosphonates and amino acids, specifically aminocarboxylic acids, added thereto as stabilizers. The invention also relates to a therapeutic method for the treatment of arthrosis by intraarticular administration of the compositions into the body of human beings and animals.

12 Claims, No Drawings

PHARMACEUTICAL COMPOSITIONS BASED ON DIPHOSPHONATES FOR THE TREATMENT OF ARTHROSIS AND OSTEOARTHRITIS

This application is a continuation-in-part of U.S. Ser. No. 866,235, filed May 22, 1986, now abandoned.

The present invention relates to novel compositions particularly useful for the treatment of arthrosis. The invention also relates to a novel method for the treatment of arthrosis.

It is known that arthrosis is a degenerative disease which involves the articular structures of the living body. Although in the past arthrosis has been considered a senility phenomon, i.e. due to the ageing of the articular structures, today clinical studies have also identified cases of appearance of arthrosis even at a relatively young age. A variation of arthrosis due to age comprising the forms of secondary arthrosis connected to age is also known.

Thus, a distinction must be made between primary arthrosis connected to an intrinsic disease of the articular structures and secondary arthrosis connected to factors which are extrinsic with respect to the articular structure itself. Doctors in general agree that arthrosis is an extremely widespread disease, certainly a very common disease among people who have suffered an injury of the joints. The frequency increases with the age to such an extent that practically everybody is affected.

Morphological researches have shown that the first alterations involve the surface cartilagenous layers in the zone of the joints, with a depolymerization and an increase of cartilagenous mucopolysaccharides. The latter are accompanied by physicochemical alterations of the collagenous fibers which become less resistant and finally break the resistance of the cartilage. This phenomenon is accompanied by a chondrocitary reaction which denotes an attempt of compensation for the reconstruction of the altered structures.

In general arthrosis is due to mechanisms which give rise to cartilagenous injuries. In fact, it has been ascertained that the various etiological factors after exceeding a certain damaging threshold, liberate a series of substances mediators from the cells of the tissues which are noxious to the articular structures.

The liberation of these mediators may directly induce a damaging action or activate the liberation of other mediators, mostly degenerative enzymes, contained in the cartilagenous and sinovial structures. The result is that also a phlogistic event occurs as a specific and secondary reaction, with the intervention of polynucleate cells and the liberation into the articular cavity from their lithic mediators which can act both directly and by activating the prostaglandinic systems.

As a consequence of the foregoing, extremely disabling conditions arise, accompanied by highly painful symptoms which may be classified on the basis of the degree of the existing alterations. The conditions are evaluated on the basis of the inhibition of motion, radiographic data, the composition of the sinovial liquid and, more recently, the arthroscopic reports.

The therapeutic methods used up to the present have proved to be insufficient to treat these diseases, and the substances used, such as analgesics, the non-steroidal antiphlogistics, and steroids, besides being simply symptomatic, have proved to create serious damaging side effects.

It is therefore an object of this invention to provide a composition and a new method for the treatment of disabling conditions connected with articular arthrosic and osteoarthritic phenomena.

The crux of the present invention resides in providing compositions containing as the active ingredient a diphosphonate of general formula

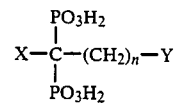

in which
X=OH, Cl, F, H
Y=NH$_2$, Cl, F, H and
n=0 to 5, with n>1 when Y=NH$_2$,
for the preparation of a medicament for the treatment of the arthrosis. The compositions contain an amino acid in the amount of 0.5–15% weight/volume, as a stabilizer. Specifically the amino acid is an aminocarboxylic acid, that is one of the essential amino acids.

According to one embodiment, this invention consists of a composition comprising an effective and non-toxic dose of sodium salt of dichloromethanediphosphonic acid in a suitable solvent to be administered by intraarticular route.

The sodium salt of dichloromethanediphosphonic acid and the other diphosphonates mentioned hereinabove represent a category of known substances which have been used up to the present for the prevention and the treatment of certain pathological situations in animals and in men, connected with an abnormal metabolism of calcium and phosphates.

According to the prior art, these conditions include the osteoporosis, the Paget disease, the ossifying myositis, the chondrocalcinosis, the artherosclerosis and other conditions induced by the abnormal mobilization or deposition of the calcium. For this purpose the diphosphonates have been utilized up to the present time for oral, intramuscular and intravenous administrations, sometimes in extremely high dosages up to 500 mg per dose by the intravenous route and 2–3 g per dose by oral route daily, with non-negligible collateral effects.

According to the present invention the salt of dichloromethanediphosphonic acid is successfully used in the treatment of arthrosis by employing a new route of intraarticular administration and extremely low and non-toxic concentration of the product.

Probably the mechanism of action consists of humoral effects, that is inhibition of the prostaglandins, of the lactate synthesis and cellular effects that is increase of the synthesis of the proteoglycans.

According to the invention, the necessary doses of sodium salt of dichloromethanediphosphonic acid or of the other diphosphonates, may obviously vary according to the seriousness of the conditions, the advisable duration of the treatment, as well as the various types of the diphosphonate used.

Generally, concentrations of sodium salt of dichloromethanediphosphonic acid between 0.1 and 10 mgs for each administration are suitable, and the dosages of sodium etidronate and the hydroxypentandiphosphonate are in the same range.

In the case of aminoderivatives, in view of their higher activity and toxicity, it is necessary to employ lower dosages between 0.01 and 1 mg each administration.

The intraarticular administration is carried out by employing aqueous solutions of the alkyliden-diphosphonic acids or their salts, preferably of alkaline-earth or alkali metals, preferably sodium, at concentrations varying between 0.01 mg–10 mg with pH between 4.5 and 7.5. The aminocarboxylic acid, in the amount of 0.5–15% weight/volume, is then added to the compositions according to the invention but is not added to the solutions used for comparison. The solutions are isotonized with the addition of sodium chloride and other suitable excipients, preferably glucose. In some cases, preservatives, preferably methyl-p-hydroxy-benzoate and analgesic agents preferably lidocaine chlorhydrate are also added.

Subsequently, samples of all the solutions (inclusive those which have to be lyophilized are subjected to accelerated stability tests (Garrett E. R., J.A.P.A.S., 44, 515). In agreement with the literature for various diphosphonic acids, (Bikman B. I., Urinovich E. M. and Coll., Zh Neorg. Khim 1973, 18 (9), 2406–9; Burton D. J. Pietrzyk D. J. and Coll., J. Fluorine Chem. 1982, 20 (5) 61726) all the tested alkilidendiphosphonic acids have proved to be perfectly thermostable.

After months of storage at ambient temperature sheltered from the light, the solutions without the stabilizer introduced into vials have evidenced the presence of bodies on the bottom, and especially those which have lower concentrations even though their titer in general had not changed. We have, however, noticed that no negative action on the stability of the solutions could be ascribed to the p-hydroxy-benzoates, the buffers and the isotonizing agents.

Surprisingly all the solutions, at any concentration of the various alkyliden-diphosphonic acids used, which have been prepared with the addition of aminocarboxylic acid as support substances for the lyophilization, have proved to be stable. Support substances for the lyophilization are substances which are used as excipients to increase the volume of the final lyophilizate.

We have therefore prepared solutions containing different quantities of amino acids preferably glycine, lysine or alanine as stabilizers, and have ascertained the stability of these liquid preparations over a prolonged period of time.

In this manner a method for the preparation of solutions in which no precipitation takes place and which, by suitably dosing the quantity of amino acids, may be lyophilized, has been provided.

Some pharmaceutical formulations suitable for use by intraarticular route, which illustrate the invention, are described in the following examples which, however, should in no way be considered as limiting.

EXAMPLE 1

Sodium salt of dichloromethanediphosphonic acid solution for intraarticular use

Sodium salt of dichloromethanediphosphonic acid: mg 1,000
10% acetic acid: mg 2,250
Annhydrous sodium hydroxide: mg 1,520
Glycine: mg 15,000
Purified water, quantity sufficient to obtain pH 5.65: ml 1,000

Compositions substantially identical to those of Example 1 may be prepared also with the salts of the 3-amino-1-hydroxypropylidene-1, 1-diphosphonic (AHPrBP), 4-amino-1-hydroxybutylidene-1, 1-diphosphonic (AHBuBP), 5-amino-1-hydroxypentylidene-1, 1-diphosphonic (AHPeBP) and 6-amino-1-hydroxyethylidene-1, 1-diphosphonic (AHEBP) acids and the difluoromethylenediphosphonic ($Fl_2MBP$) acid.

The concentrations of the active principle may vary between 0.1 and 10 mg/cc for the compounds AHPeBP and $Fl_2MBP$. The concentration of the active principle may vary between 0.01 and 1 mg/ml for the compounds AHPrBP, AHBuBP and AHEBP.

EXAMPLE II

Sodium salt of dichloromethanediphosphonic acid solution for peri-articular use

Sodium salt of dichloromethanediphosphonic acid: mg 1,000
Anhydrous sodium hydroxide: mg 0,325
Lidocaine chlorhydrate: mg 1,000
Glycine: mg 20,000
Water in amount sufficient to obtain pH 6.45: mg 1,000

Various solutions similar to those of the solution of Example II may be prepared by using the acids AHPrBP, AHBuBP, AHPeBP, AHEBP instead of dichloromethanediphosphonic acid.

The concentration of the active principle for all the acids, inclusive the dichloromethanediphosphonic acid, may vary as stated hereinabove in Example I.

EXAMPLE III

Solution for peri- and intraarticular use, available in a container with the lyophilized material (A)+a vial of solvent (B)

A—Container with lyophilized material
Sodium salt of dichloromethanediphosphonic acid: mg 0.05
Glycine: mg 125,00
Procaine chlorhydrate: mg 10,00
Water, a quantity sufficient to obtain pH 6.0: ml 0.50
Solution (A) is subjected to lyophilization
B—vial of solvent
Methyl p-hydroxybenzoate: mg 2,500
Anhydrous acetic acid: mg 2,250
Anhydrous sodium hydroxide: mg 1,525
Water, in a quantity sufficient to obtain pH 6.0: ml 5,000

Compositions substantially corresponding to those indicated in "A" may be obtained by substituting the sodium dichloromethanediphosphonic acid by a sodium salt of AHPrBP, AHPeBP, AHEBP, $Fl_2MBP$ and, generally, of any diphosphonic acid. The concentration of the active principle may vary as stated hereinabove, under Example I.

For the purpose of showing the superiority of compositions containing the aminocarboxylic acid as a stabilizer, comparative experiments have been carried out. A solution (a) of $Cl_2MBP$ according to Example 1 of the specification has been prepared.

$Cl_2MBP$: mg 100,0
10% acetic acid: mg 225,0
Anhydrous sodium hydroxide: mg 152,0
Glycine: mg 1500,0
Purified water sufficient to obtain pH 5.65: ml 100,0

On the same day solutions (a), (b), (c), (d) have been prepared.

Solution (b) was identical to (a) but 1500 mg of lysine was added.

Solution (c) was identical to (a) but 1500 mg of alanine was added.

Solution (d) was identical to (a) but it only contained Cl₂MBP acetic acid, aqueous sodium hydroxide and purified water.

To the solution (b) it was necessary to add some HCl N to bring the pH to 5.65; to the solution (d), on the contrary, some NaOH N was added to bring the pH to the same value.

Out of each of the four above-mentioned solutions, were prepared ten vials of 2 ml each, which were closed and placed in thermostat, in the dark, for 8 weeks. At the end of this period of time, it was found that:

the contents of all the ten vials of the solutions (a), (b) and (c) was perfectly clear, with no trace of precipitate;

the contents of six vials of solution (d) was visibly turbid, and so was the one of the other four vials which had also traces of precipitate at the bottom;

Clearly, aminocarboxylic acids stabilize the compositions according to the invention.

The concentrations of the active ingredients may vary.

The effectiveness of the formulations provided by the present invention for the treatment of the arthrosis has been demonstrated by an accurate research carried out in hospital conditions.

The patients admitted for the test were men and women, aged between 65 and 80 years, with a serious form of arthrosis of the ilium or the knee or of the scapulo-humeral region in a pre-degenerative stage, and for whom, due to the lack of other valuable therapeutic means, a surgical operation had been suggested. The stage of the conditions was evaluated by observing the tumefaction, the alterations of the sinovial liquid, the degree of the motorial limitations and the radiographic reports directed to the articular rima and to the arthroscopic report carried out by a complex methodology capable of providing also photographic images.

The patients subjected to the research were excluded from any other type of treatment and were treated with diphosphonates by intraarticular route with doses between 10 and 100 mcg in a volume from 0,5 to 2 ml. The above and other parameters concerning the tolerability were evaluated at the time 0 and then after 7–10 days and also after 14–20 days at the second and third administration of the composition.

Surprisingly, the analyses carried out have proved that about 60% of the patients have obtained a striking improvement with a normalization of the objective parameters and a return to an almost normal articular functionality when considering the age of the patients. Among the patients who have received only a partial benefit, the repetition of the cycle of treatment and the administration of the composition by intramuscular route with daily doses of 100 mg, or at alternate days, for 15–30 days have led to a further increase of the percentage of the patients whose conditions have improved.

In all cases the tolerability of the medicament was perfect and without any modification of the bihumoral parameters which were examined.

What is claimed is:

1. A pharmaceutical composition for the treatment of arthrosis in a human or an animal which essentially consists of an aqueous solution of pH 4.5–5.65 containing 0.01–10 mgs per unit dose of a diphosphonic acid as the active ingredient of formula

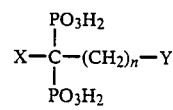

wherein
 X=OH, Cl, F, H
 Y=NH₂, Cl, F, H
 n=an integer from 0 to 5, with the proviso that n is greater than 1 if Y=NH₂
or pharmaceutically acceptable salt, thereof, and at least one aminocarboxylic acid as stabilizer.

2. The pharmaceutical composition according to claim 1 wherein said aminocarboxylic acid is glycine, lysine or alanine.

3. The composition according to claim 2 wherein the active ingredient is dichloromethylenediphosphonic acid or a pharmaceutically acceptable salt thereof.

4. The composition according to claim 1 wherein the active ingredient is 3-amino-1 hydroxypropylidene-1,1-diphosphonic acid or a pharmaceutically acceptable salt thereof.

5. The composition according to claim 1 wherein the active ingredient is 4-amino-1 hydroxybutylidene-1,1-diphosphonic acid or a pharmaceutically acceptable salt thereof.

6. The composition according to claim 1 wherein the active ingredient is 5-amino-1 hydroxypentylidene-1,1-diphosphonic acid or a pharmaceutically acceptable salt thereof.

7. The composition according to claim 1 wherein the active ingredient is 6-amino-1 hydroxyethylidene-1,1-diphosphonic acid or a pharmaceutically acceptable salt thereof.

8. The composition according to claim 1 wherein the active ingredient is ethane-1-hydroxy-1-diphosphonic acid or a pharmaceutically acceptable salt thereof.

9. The composition according to claim 1 wherein the active ingredient is difluoromethandiphosphonic acid or a pharmaceutically acceptable salt thereof.

10. The composition according to claim 1 wherein the active ingredient is pentane-1-hydroxy-1, 1 diphosphonic acid or a pharmaceutically acceptable salt thereof.

11. The method of treating arthrosis in a human or an animal which consists of administering to said human or animal in need of treatment by the intraarticular route an aqueous solution of pH 4.5–5.65 containing as the active ingredient 0.01–10 mgs per unit dose of a diphosphonic acid of formula

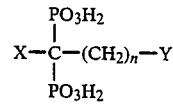

wherein
 X=OH, Cl, F, H
 Y=NH₂, Cl, F, H
 n=an integer from 0 to 5, with the proviso that n is greater than 1 if Y=NH₂
or a pharmaceutically acceptable salt thereof; and, as a stabilizer an aminocarboxylic acid.

12. The method according to claim 11 wherein said aminocarboxylic acid is glycine, lysine or alanine.

* * * * *